United States Patent
Pini et al.

(10) Patent No.: US 8,921,308 B2
(45) Date of Patent: Dec. 30, 2014

(54) ANTIMICROBIAL PEPTIDE, BRANCHED FORMS THEREOF AND THEIR USE IN THE TREATMENT OF BACTERIA INFECTIONS

(75) Inventors: Alessandro Pini, Siena (IT); Chiara Falciani, Siena (IT); Luisa Bracci, Siena (IT)

(73) Assignee: Setlance S.R.L., Siena (IT)

( * ) Notice: Subject to any disclaimer, the term of this patent is extended or adjusted under 35 U.S.C. 154(b) by 0 days.

(21) Appl. No.: 13/811,039

(22) PCT Filed: Jul. 11, 2011

(86) PCT No.: PCT/EP2011/003446
§ 371 (c)(1),
(2), (4) Date: Jan. 18, 2013

(87) PCT Pub. No.: WO2012/010266
PCT Pub. Date: Jan. 26, 2012

(65) Prior Publication Data
US 2013/0130969 A1    May 23, 2013

(30) Foreign Application Priority Data
Jul. 23, 2010    (EP) .................................... 10170639

(51) Int. Cl.
| | | |
|---|---|---|
| *A61K 38/08* | (2006.01) | |
| *C07K 7/06* | (2006.01) | |
| *A61P 31/04* | (2006.01) | |
| *C07K 17/08* | (2006.01) | |
| *C07K 17/10* | (2006.01) | |
| *C11D 3/38* | (2006.01) | |
| *C07K 17/02* | (2006.01) | |
| *A23L 3/3526* | (2006.01) | |
| *C11D 3/48* | (2006.01) | |
| *A61K 38/00* | (2006.01) | |

(52) U.S. Cl.
CPC ................. *C07K 17/10* (2013.01); *C07K 17/08* (2013.01); *C07K 7/06* (2013.01); *C11D 3/38* (2013.01); *C07K 17/02* (2013.01); *A23L 3/3526* (2013.01); *A61K 38/00* (2013.01); *C11D 3/48* (2013.01)
USPC .......................................... 514/2.4; 530/328

(58) Field of Classification Search
CPC ........ A23L 3/3526; A61K 38/00; C07K 7/06; C07K 17/10; C07K 17/02; C07K 17/08; C11D 3/48; C11D 3/38
See application file for complete search history.

(56) References Cited

FOREIGN PATENT DOCUMENTS

WO    WO 2009/146885 A2 * 12/2009    ............. A61K 47/48
WO    2010/038220 A1    4/2010

OTHER PUBLICATIONS

Adessi et al, Converting a Peptide into a Drug: Strategies to Improve Stability and Bioavailability, Current Medicinal Chemistry, 2002, 9, pp. 963-978.*
International Search Report issued in counterpart International PCT Application No. PCT/EP2011/003446, Dec. 2011.
Pini, et al. "A novel tetrabranched antimicrobial peptide that neutralizes bacterial lipopolysaccharide and prevents septic shock in vivo," The FASEB Journal, vol. 24, No. 4, pp. 1015-1022, Apr. 2010 (XP002605087).
Pini, et al., "Branched Peptides as Therapeutics," Current Protein and Peptide Science, vol. 9, No. 5, pp. 468-477, Oct. 1, 2008 (XP009129099).
Pini, et al. "Characterization of the branched antimicrobial peptide M6 by analyzing its mechanisms of action and in vivo toxicity," Journal of Peptide Science, vol. 13, pp. 393-399, May 2007 (XP002548817).
Scholl, et al. "Dendritic and hyperbranched polyamides," Progress in Polymer Science, vol. 34, No. 1, pp. 24-61, Jan. 2009 (XP025869980).

* cited by examiner

*Primary Examiner* — Julie Ha
*Assistant Examiner* — Li Ni Komatsu
(74) *Attorney, Agent, or Firm* — Silvia Salvadori, P.C.

(57) ABSTRACT

The instant invention refers to an antibacterial peptide with all amino acids in D-configuration, possessing strong antimicrobial activity against Gram-negative and Gram-positive bacteria and *Candida* strains. The peptide can be in linear form multimerised on a skeleton of polyacrylamide, of dextrane units or on a skeleton of ethylene glycol units. The peptide is resistant proteolysis especially when synthesized in the tetra-branched form where identical peptide sequences are linked together by an appropriate molecular scaffold.

12 Claims, 5 Drawing Sheets

Figure 1:
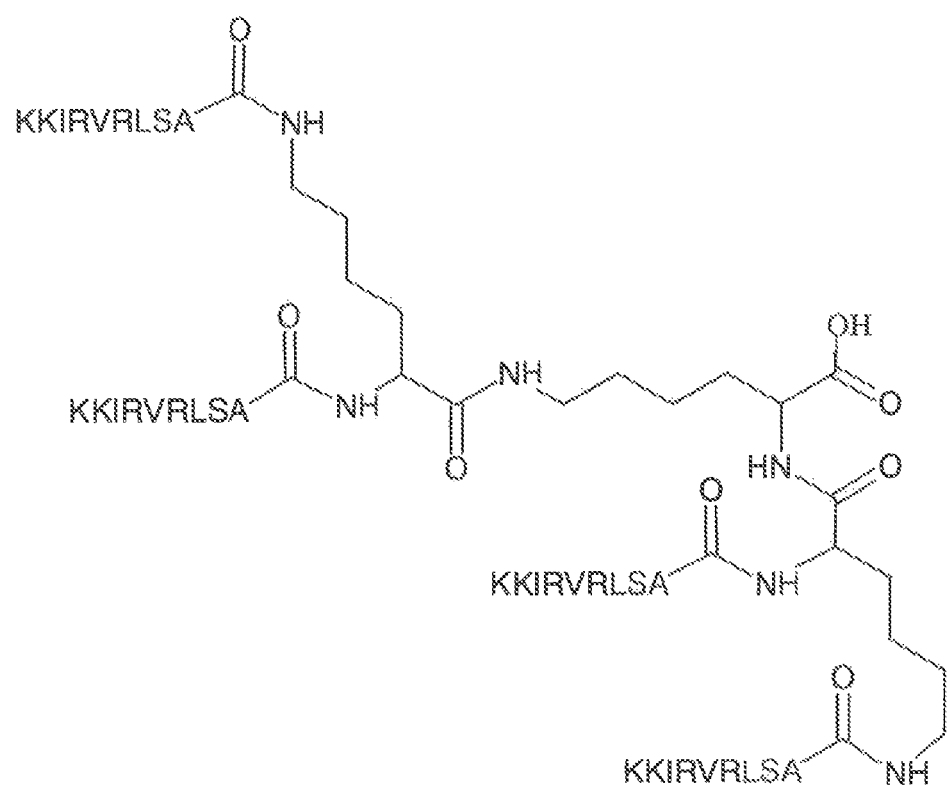

A L-M33 incubated 1 hour with Aureolysin    B D-M33 incubated 24 hours with Aureolysin

SEQUENCE LISTING

```
<160> NUMBER OF SEQ ID NOS: 1

<210> SEQ ID NO 1
<211> LENGTH: 9
<212> TYPE: PRT
<213> ORGANISM: Unknown
<220> FEATURE:
<223> OTHER INFORMATION: artificial peptide
<220> FEATURE:
<221> NAME/KEY: MISC_FEATURE
<222> LOCATION: (1)..(9)
<223> OTHER INFORMATION: amino acids in D-configuration

<400> SEQUENCE: 1

Lys Lys Ile Arg Val Arg Leu Ser Ala
1               5
```

ANTIMICROBIAL PEPTIDE, BRANCHED FORMS THEREOF AND THEIR USE IN THE TREATMENT OF BACTERIA INFECTIONS

This application is a U.S. national stage of PCT/EP2011/003446 filed on Jul. 11, 2011, which claims priority to and the benefit of European Application No. 10170639.8, filed on Jul. 23, 2010, the contents of which are incorporated herein by reference.

TECHNICAL FIELD OF THE INVENTION

The instant invention refers to a peptide with strong antimicrobial activity against Gram-negative and Gran-positive bacteria and *Candida* strains, all the amino acids of the peptide sequence being in D-configuration. The peptide is particularly resistant to proteolysis when synthesized in the tetra-branched form where identical peptide sequences are linked together by an appropriate molecular scaffold. This form makes the peptide particularly suitable for clinical applications.

BACKGROUND ART

The growing emergency of multi-drug resistant-bacteria is a global concern, mostly in those countries where antibiotics are widely used in clinics. A number of pathogens like *Staphylococcus aureus, Staphylococcus epidermidis, Mycobacterium tuberculosis*, some enterococci, *Pseudomonas aeruginosa* and many other bacteria have developed resistance against most traditional antibiotics as well as against those of new generation (Wenzel and Edmond 2000). It has therefore become increasingly important to develop new antibiotics. This demand urges the community of researchers and the pharmaceutical companies to consider new antimicrobial agents. Antimicrobial peptides are considered one of the best alternative to traditional antibiotics which generally cause the selection of resistant bacteria (Hancock and Sahl, 2006). Most antibacterial peptides are components of the innate immunity of animals, including humans, plants and fungi (Zasloff, 2002). They usually consist of 6-50 amino acid residues and have a positive net charge. Cationic peptides interact selectively with anionic bacterial membranes and with other negatively charged structures such as LPS and DNA. Eukaryotic membranes, in their external layer, are normally less negatively charged than bacteria's, and, differently from bacterial membrane, they are also stabilized by cholesterol molecules. These differences are the basis of cationic peptides' specificity. The mechanism of action of cationic antimicrobial peptides is consequently due to their specific binding to bacterial membranes, which provokes cell permeation and, in some cases, metabolic pathways inhibition.

Many studies then, aimed to the identification and characterization of antimicrobial peptide sequences by studying their mechanism of action, their toxicity for eukaryotic cells and their therapeutic efficacy when administered topically or systemically. Unfortunately, two main problems hindered the development of antimicrobial peptide drugs so far. The first is that selectivity of natural antimicrobial peptides for bacteria is generally too low and they appear to be very toxic for eukaryotic cells, particularly erythrocytes, generating a high level of haemolysis. The second is linked to the generally short half-life of peptides in vivo. These are the main reasons for which only few cationic peptides reached the market in the last 10 years (polymyxin and daptomycin are two successful examples).

A few years ago, researchers began to concentrate on the identification of novel peptide sequences of non-natural origin, selected in the laboratory by rational design or screening of combinatorial libraries. The aim was to find peptides with better biological properties in terms of general toxicity and specificity for bacteria and improved half-life for drug development.

In the inventors' laboratory, non-natural peptide sequences were identified, which showed a strong antimicrobial activity especially against Gram-negative bacteria (Pini et al, 2005; Pini et al., 2007; Pini et al., 2010). The last improved version of these peptides was called M33 (sequence KKIRVRLSA, SEQ ID NO: 1; WO 2010/038220 A1) and it was tested in vitro for its capability to neutralize bacterial LPS and in vivo for its antibacterial and anti-inflammatory activity in sepsis animal models (Pini et al., 2010). Peptide M33 appeared selective for Gram-negative bacteria with a slight activity against only two strains of the Gram-positive *Staphylococcus aureus*. The peptide M33 was used and described in Pini et al., 2010 and in WO2010/038220A1 always with amino acids in L configuration (L-M33). Surprisingly, the synthesis of the same peptide sequence wide all the amino acids in D-configuration (D-M33) produced not only a better activity for some Gram-negative bacteria but also a strong activity against a panel of Gram-positive bacteria and fungi for which the L-M33 was not active at all. This result is completely unexpected, in that substitution of L-amino acids with their D configuration is known to increase peptide stability but the effect on peptide selectivity was not predictable.

DESCRIPTION OF INVENTION

It is an object of the present invention the peptide sequence KKIRVRLSA, SEQ ID NO: 1 characterized in that all amino acids are in D-configuration (hereinafter referred to as D-M33), either in linear (i.e. monomeric) form or multimerised (i.e. dendrimeric or branched) on a skeleton of polyacrylamide, on a skeleton of dextrane units or on a skeleton of ethylene glycol units, or, preferably, on a scaffold that follows the general formula (I)

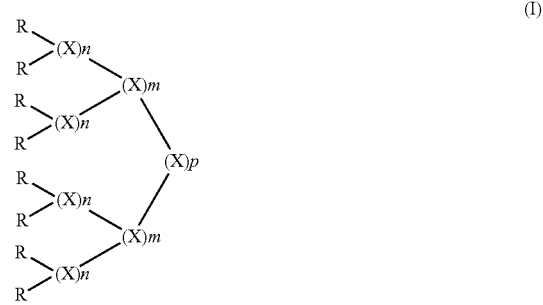

in which R is the peptide as claimed in claim 1 and described above; X is an at least bifunctional molecule (in R or S configuration if asymmetric), and:

m=n=0 and p=1, whereby the peptide is a dimer of formula (Ia);

or m=1, p=1 and n=0, whereby the peptide is a tetramer of formula (Ib);

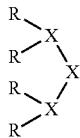
(Ib)

or m=n=p=1, whereby the peptide is an octamer of formula (Ic).

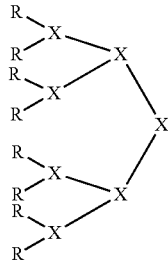
(Ic)

The X group preferably comprises at least two functional amino groups, which are preferably provided by diaminoacids such as ornithine, nor-lysine, amino alanine or diaminopropionic acid, either alone or linked to different aminoacid residues by a peptidic bond, particularly β-Ala.

Alternatively, the X group is selected from the group consisting of aspartic acid, glutamic acid, propylene glycol, succinic acid, a diisocyanate, or N,N-bis(3-aminopropyl)-glycine (BAPG) or other dendrimeric polyamine or polyacidic molecules.

Dendrimeric polyamine-based scaffolds according to the invention can be prepared following the procedures described in Tam, 1988; Tam et al., 2002, Falciani et al., 2005; Stasko and Schoenfisch, 2006; Rudovskýet al., 2006, which are herein incorporated by reference.

It is a further object of the invention the peptide as described above for medical use, preferably as an antibacterial medicament.

It is a further object of the invention a pharmaceutical composition comprising a pharmaceutically acceptable and effective amount of the peptide as described above. The composition may be in the form of an injectable solution for systemic administration, preferably in the form of an injectable solution for use as detoxifying agent for LPS neutralization, still preferably in the form of eyewash, mouth wash, ointment, aerosol, or solution for topical administration.

It is a further object of the invention a disinfectant and/or detergent preparation with antibacterial activity comprising the peptide of the invention.

It is a further object of the invention the use of the invention peptide as a preservative for the preparation of food products and/or of cosmetic products and/or of homeopathic products.

It is another object of the present invention the use of such peptide as antimicrobial agent for medical, veterinary and agronomic applications.

The invention peptide is advantageous compared with the already described M6 or L-M33 peptides disclosed, respectively, in EP 1 789 436 B1 and in WO 2010/038220 A1, for its better efficacy against Gram-negative and especially for its activity against Gram-positive bacteria as shown in the following tables. This crucial feature, along with its very encouraging antimicrobial activity, makes D-M33 peptide an optimal candidate for the development of new antibacterial drugs for the treatment of infections caused by Gram-positive bacteria.

The invention will be now described by non limiting examples referring to the following figures:

FIG. 1

Formula of the tetra-branched M33 (L, or D) peptide where functional amino groups are lysine amino acids.

FIG. 2

Effect of tetra-branched L-M33, D-M33 and monomeric Indolicidin on haemolysis of human erythrocytes. The figures show the haemolytic activity of the three peptides on human erythrocytes evaluated by means of erythrocyte osmotic resistance of Parpart method in NaCl. The percentage of haemolysis is calculated by means of a calibration curve obtained by incubating erythrocytes with increasing concentrations of NaCl. After 30 min of incubation, L-M33 and D-M33 (at the maximum concentration tested) displayed only a weak haemolytic activity (<5%). The natural antimicrobial peptide Indolicidin appears more haemolytic. The percentage of haemolysis of untreated blood after 19 hours (control) is very limited (<1%).

FIG. 3

Figure 3:
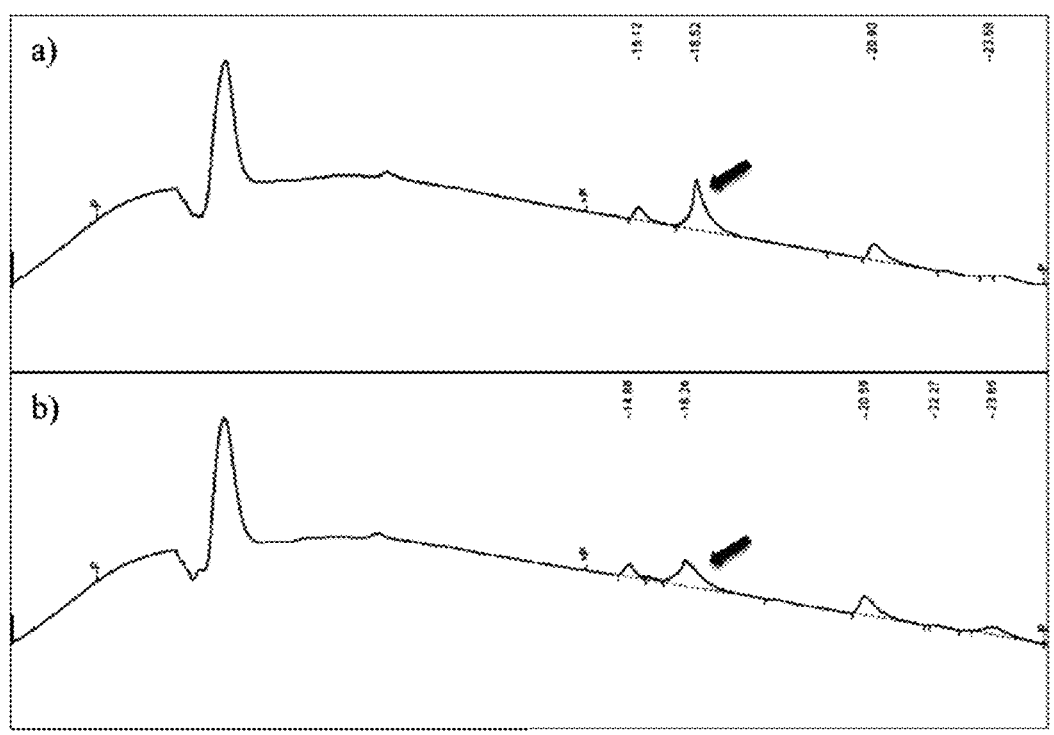

HPLC profile of tetra-branched peptide D-M33 incubated in human serum at 0 h (FIG. 3A) and 24 h (FIG. 3B). Retention time of D-M33 is indicated by an arrow.

FIG. 4

In vivo antibacterial activity of tetra-branched D-M33 peptide. Balb-c mice (20 g) were intra-peritoneally injected with a lethal amount of E. coli TG1 cells ($1 \times 10^9$ CFU). Continuous line (Ctr) indicates mice only injected ip with bacteria and no D-M33. Broken line indicates mice injected ip with bacteria and a single injection of D-M33 peptide 10 mg/Kg 1 hour later.

$P<0.05$.

FIG. 5

In vivo antibacterial activity of tetra-branched D-M33 peptide. Balb-c mice (20 g) were intra-peritoneally injected with a lethal amount of S. aureus USA 300 cells ($5 \times 10^6$ CFU) mixed in a 7% mucin solution. Control line (Ctr) indicates mice only injected ip with bacteria and no D-M33. D-M33 line indicates mice injected ip with bacteria and a single injection of D-M33 peptide 25 mg/Kg 1 hour later. $P<0.05$.

FIG. 6

HPLC profiles of tetra-branched peptides L-M33 (A) and D-M33 (B) after incubation with the protease Aureolysin derived from S. aureus. L-M33 appeared degraded after only 1 hour of incubation with the enzyme (see highlighted peaks in A). D-M33 did not show degradation after 24 hours of incubation.

DETAILED DESCRIPTION OF THE INVENTION

Peptide Synthesis

Monomeric peptide was synthesized as peptide amide by an automated synthesizer (MultiSynTech, Witten; Germany) on a Rink Amide MBHA resin (Nova Biochem) using 9-fluorenytmethoxycarbonyl (Fmoc) chemistry and O-(benzottriazol-1-yl)-N,N,N',N'-tetramethyluronium hexafluorophosphate/1,3-diisopropylethylamine activation. Branched peptide molecules (MAPs) were synthesized on Fmoc$_4$-Lys$_2$-Lys-βAla Wang resin. Side chain protecting groups were trityl for Gln tert-butoxycarbonyl for Lys, 2, 4,6,7-pentamethyldihydrobenzofuran-5-sullonyl for Arg, and tert-butyl ether for Ser. Peptides were then cleaved from the resin and deprotected with trifluoroacetic acid containing water and triisopropylsilane (95/2.5,/2.5). Crude peptides were purified by reversed-phase chromatography on a Vydac C18 column. TFAcetate-acetate counter ion exchange is performed on a ion-exchange resin (AG1-X8 acetate, Biorad) and the peptides are lyophilized and isolated as peptide $CH_3COO$—. Identity and purity of final products was confirmed by ETTAN™ MALDI-TOF mass spectrometry (MS) (Amersham Biosciences).

The structure of a tetra-branched M33 peptide as described above is reported in FIG. 1.

Antibacterial Activity of Tetra-Branched Peptides

Minimum Inhibitory Concentration (MIC) was determined by a standard microdilution assay as recommended by the National Committee for Clinical Laboratory Standards (NCCLS) using cation-supplemented Mueller-Hinton (MH) broth (Oxoid Ltd. Basingstoke, UK) and a bacterial inoculum of $5 \times 10^4$ CFU per well, in a final volume of 100 µl. Results were recorded by visual inspection after 24 h of incubation at 37° C.

Peptide MICs were determined against strains of several bacterial species, including Gram-negative and Gram-positive pathogens (Table 1 and 2). Activity of tetra-branched D-M33 was retained against MDR strains with various resistance mechanisms (such as extended-spectrum beta-lactamases and carbapenemases), including MDR P. aeruginosa strains from CF patients. The antimicrobial activity of tetra-branched D-M33 appeared slightly better with respect to tetra-branched L-M33 for MDR strains of Pseudomonas and one strain of Klebsiella and sensitively better respect to tetra-branched L-M33 for the two strains of Staphyloccoccus aureus reported in Table 1.

TABLE 1

| Bacteria species and strains | Features and resistances | L-M33 (µM) | D-M33 (µM) |
|---|---|---|---|
| P. aeruginosa PAO-1 | reference strain | 1.5 | 0.7 |
| P. aeruginosa VenM rugosa 05/04/2005^ | FQ' AG' ESC' NEM' | 3 | 0.7 |
| P. aeruginosa OGB6-1^ | FQ' AG' ESC' NEM' (MBL/IMP-13) | 1.5 | 0.7 |
| Klebsiella pneumoniae ATCC 13833 | Reference strain | 1.5 | 0.7 |
| Klebsiella pneumoniae FIPP | FQ' AG' ESC' NEM' (KPC-3) | 1.5 | 3 |
| E. coli ATCC 25922* | reference strain | 1.5 | 1.5 |
| E. coli W03BG0025* | FQ' AG' ESC' (ESBL/CTX-M-15) | 0.7 | 1.5 |
| Enterobacter cloacae W03AN0041 | ESC' (ESBL/SHV-12) | 0.7 | 3 |
| Acinotebacter baumannii RUH 134 | Reference strain, European clone II | 1.5 | 3 |
| Acinotebacter baumannii RUH 875 | Reference strain, European clone II | 1.5 | 3 |
| Staphylococcus aureus MU 50 ATCC 700699 | Reference strain, vancomycin resistant | 6 | 3 |
| Staphylococcus aureus 3851 | Vancomycin intermediate | 6 | 0.7 |

Tested strains included either reference strains (indicated) or clinical isolates (mostly showing an MDR phenotype);
relevant resistance traits and resistance mechanisms are indicated:
FQ', resistant to fluoroquinolones;
AG', resistant to aminoglycosides (gentamicin, amikacin, and/or tobramycin);
ESC', resistant to expanded-spectrum cephalosporins;
NEM', resistance to carbapenems (imipenem and/or meropenem),
ESBL, extended spectrum β-lactamase;
MBL, metallo-β-lactamase TABLE 1-continued

| Bacteria species and strains | Features and resistances | L-M33 (µM) | D-M33 (µM) |
|---|---|---|---|

^Clinical isolates from Cystic Fibrosis patients

Minimal inhibitory concentration of tetra-branched D-M33 was consequently tested against a panel of Gram-positive bacteria and fungi for which tetra-branched L-M33 was not active at concentrations below 24 µM (Table 2). Surprisingly, tetra-branched D-M33 is active against all microorganisms tested, with the better efficacy (0.35 µM) for the strains of S. epidermidis and one strain of S. capitis. MIC of 0.35 µM was never reported for tetra-branched L-M33 against Gram-negative bacteria.

TABLE 2

| Bacteria species and strains | Features and resistances | MIC D-M33 (µM) |
|---|---|---|
| S. pneumoniae ATCC 49619 | reference strain | 6 |
| S. pneumoniae 47C12 | clinical isolate, no resistant | 12 |
| S. pneumoniae 47D22 | clinical isolate, resistant to macrolides, tetracyclin, cotrimossazole | 6 |
| S. agalactiae ATCC 13813 | reference strain | 1.5 |
| S. epidermidis ATCC 14990 | reference strain | 0.35 |
| S. epidermidis 4761/1 | clinical isolate, no resistant | 0.35 |
| S. epidermidis 6154 | clinical isolate, no resistant | 0.35 |
| S. capitis ATCC 27840 | reference strain | 0.35 |
| S. aureus ATCC 29213 | reference strain | 3 |
| S. aureus 3851 | clinical isolate, intermedium resistant to vancomycin | 1.5 |
| S. aureus Fi-Fran | clinical isolate, no resistant | 1.5 |
| E. faecalis ATCC 29212 | reference strain | 0.7 |
| E. faecalis FI74B4 VSE | clinical isolate, no resistant | 0.7 |
| E. faecium FI81B1 VRE | clinical isolate, vancomycin resistant | 0.7 |
| E. faecium FI81B2 VSE | clinical isolate, no resistant | 0.7 |
| C. glabrata ATCC 90030 | reference strain | 12 |
| C. parapsilosis ATCC 90018 | reference strain | 1.5 |
| C. albicans 9833 | clinical isolate, itraconazole resistant | 24 |
| C. tropicalis 6597 | clinical isolate, flucanonazole, itraconazole, voriconazole and 5'-fluorocitosine resistant | 12 |
| C. krusei ATCC 6268 | reference strain | 6 |

Haemolytic Activity of Tetra-Branched Peptide D-M33

Haemolysis of fresh human erythrocytes was determined using the method of Parpart, summarized as follows. A calibration curve was constructed by suspending fresh human erythrocytes in phosphate buffer (pH 7.4, 110 mM sodium phosphate) with various concentrations of NaCl and incubated for 30 min at room temperature. Samples were centrifuged at 500×g for 5 minutes, and haemoglobin release was monitored by measuring the absorbance of supernatants at 540 nm. The absorbance obtained with 0.1% NaCl corresponded to 100% lysis and that with 1% NaCl, to 0% lysis. Peptides dissolved in PBS were added to human erythrocyte solution at several concentrations. The resulting suspension was incubated separately at 37° C. for 2 h and 24 h. Release of hemoglobin was monitored by measuring the absorbance of the suspenatant at 540 nm after centrifuging and haemolysis percentage was calculated using the calibration curve.

Figure 2:
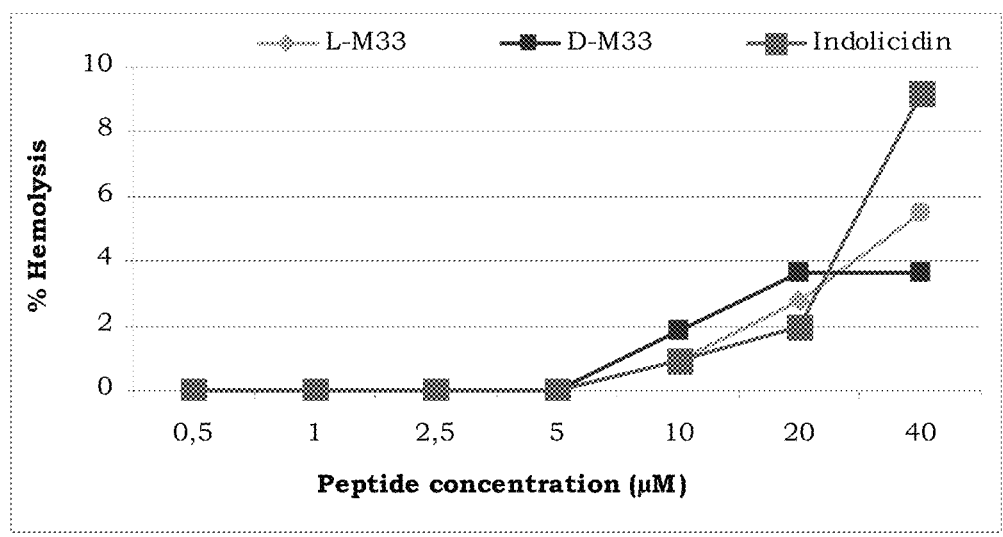

A very important feature is that, contrary to most antimicrobial peptides described so far, tetra-branched D-M33 shows a negligible haemolysis grade (FIG. 2), suggesting their possible use also through systemic administrations.

Peptide Stability

8 μl of a 1-mg/ml solution of peptides was incubated at 37° C. with 20 μl human serum (FIG. 3) or plasma. Samples withdrawn at time 0 (FIG. 3A) and after 24 h (FIG. 3B) were precipitated with 200 μl methanol, centrifuged for 1 min at 10 000×g and diluted with 800 μl 0.1% TFA in water. These solutions were analyzed by HPLC using a C18-column Controls for peptide retention time in the crude mixture were obtained by adding the same concentration of tetra-branched peptides to supernatants of plasma or serum treated with methanol and centrifuged as above, running the mixture immediately. MS analysis of the supernatant of crude solutions was performed on an ETTAN MALDI TOF mass spectrometer. The results are reported in FIG. 3.

In Vivo Antibacterial Activity

Tetra-branched D-M33 peptide was analysed for its antibacterial activity in mice infected with lethal amounts of the Gram-negative bacterium *E. coli* or the Gram-positive bacterium *S. aureus*.

The smallest number of bacteria causing 100% lethal infection (LD100) after intra-peritoneal (ip) injection was $1.5 \times 10^9$ with *E. coli* and $5 \times 10^6$ with S aureus. Bacterial LD100 killed mice in 15-24 hours. Balb-c mice were infected with the LD100 of bacteria and treated 1 hour later with the peptide by ip administration.

Figure 4:
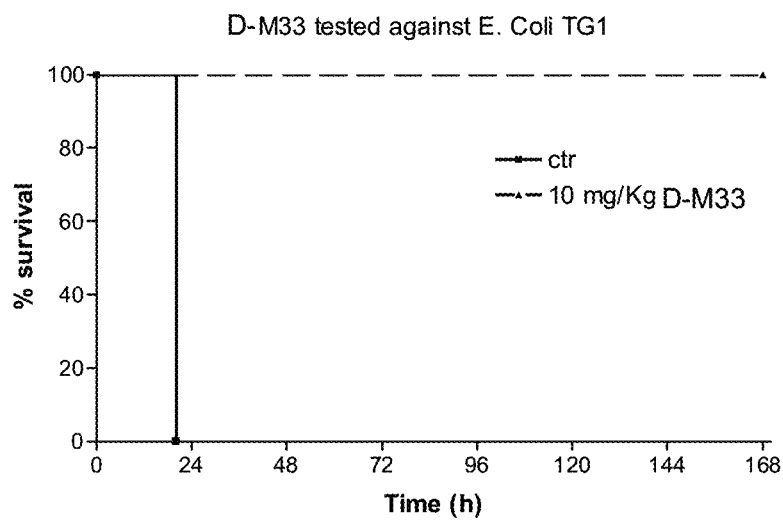
Figure 5:
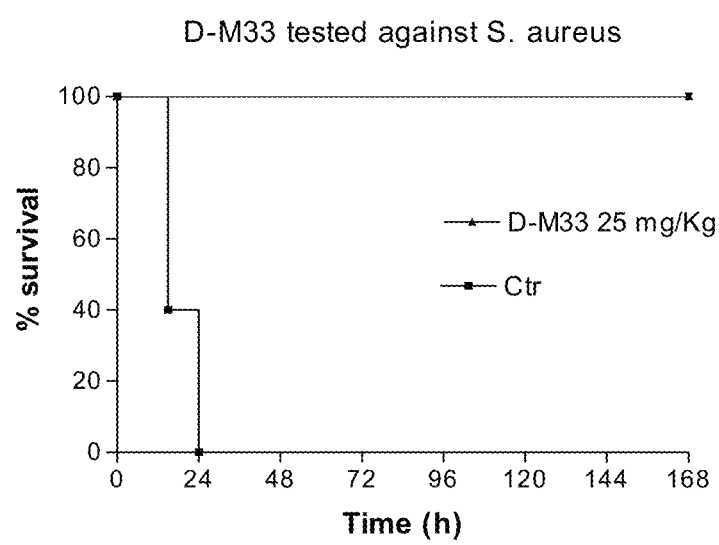

Following infection with bacteria, D-M33 protected 100% of animals from signs of sepsis and death (seven-day survival) when administered in a single dose at a concentration of 10 mg/Kg for *E. coli* (FIG. 4) and 25 mg/Kg for *S. aureus* (FIG. 5). D-M33 did not produce apparent toxicity signs in animals treated ip with a peptide dose of 100 mg/Kg (not shown), 10 time the dose reported in FIGS. 4 and 4 times the dose of FIG. 5.

Peptide Stability to Bacterial Proteases

Figure 6:
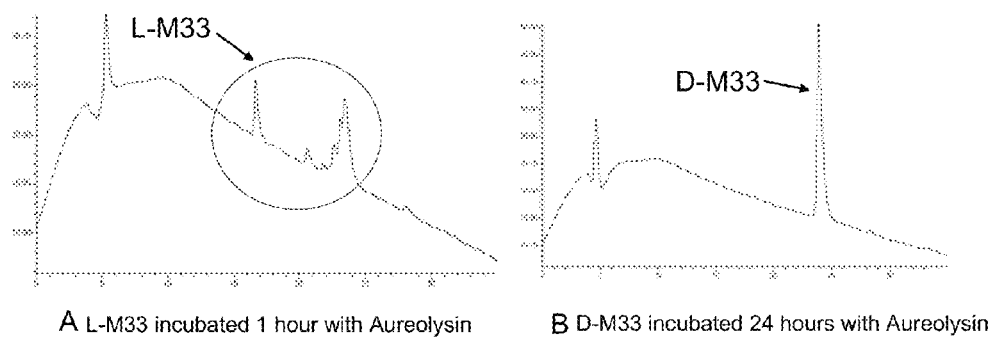

D-M33 proved more stable to bacterial proteases than L-M33. FIG. 6 shows the incubation of both peptides with the *S. aureus* protease Aureolysin, which appears particularly active against L-M33 and inactive within 24 hours against D-M33.

BIBLIOGRAPHY

Bracci L, et al., 2003, J Biol Chem, 278: 46590-5
Cornaglia G, et al., 2000, Clin Infect Dis, 31: 1119-25
Falciani C et al., 2005, Chem Biol, 69:216-21
Falciani C, et al., 2007, Chem Biol Drug Des, 69: 216-21
Hancock R E and Sahl H G, 2006, Nat Biotecnol 24: 1551-7
Pini A, et al., 2005, Antimicrob Agents Chemother, 49: 2665-72
Pini A, et al, 2007, J Pept Sci, 13:393-9
Pini A et al., 2010, FASEB J. 24:1015-1022
Stasko N A and Schoenfisch M H, 2006, J Am Chem Soc, 28:8265-71
Tam J P, 1988, Proc Natl Acad Sci, 85:5409-13
Tam J P et al., 2002, Eur J Biochem, 269:923-32
Wenzel R P and. Edmond M B, 2000, N Engl J Med 343:1961-3
Zasloff M. 2002, Nature, 415:389-95
Rudovský J et al., 2006, Bioconjug Chem, 17:975-87.

The invention claimed is:

1. An antibacterial peptide consisting of the amino acid sequence KKIRVRLSA (SEQ ID NO: 1), wherein all amino acids are in the D-configuration.

2. The peptide according to claim 1, said peptide being in the form of linear peptide.

3. The peptide according to claim 1, said peptide being multimerised on a skeleton of polyacrylamide, on a skeleton of dextrane units or on a skeleton of ethylene glycol units.

4. The peptide according to claim 1, said peptide being multimerised on a scaffold having the following formula (I)

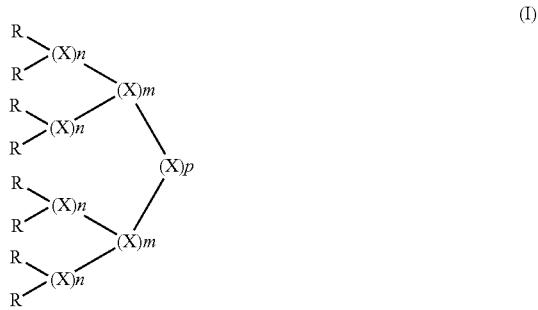

in which R is the peptide as claimed in claim 1; X is, independently from one another, an amino acid selected from lysine, ornithine, nor-lysine, amino alanine, or diaminopropionic acid and a dipeptide containing one of these amino acid; and:

m=n=0 and p=1, whereby the peptide is a dimer of formula (Ia)

(Ia)

or m=1, p=1 and n=0, whereby the peptide is a tetramer of formula (Ib)

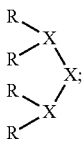

(Ib)

or m=n=p=1, whereby the peptide is an octamer of formula (Ic)

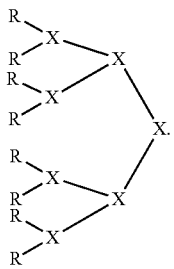

(Ic)

5. The peptide according to claim 4, wherein said peptide is as set forth by the following chemical formula:

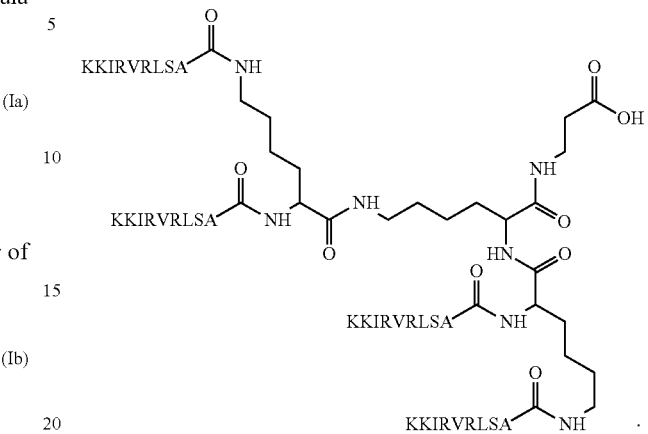

6. A medicament comprising the peptide according to claim 1.

7. An antibacterial drug comprising the peptide according to claim 1.

8. A method of treating infections caused by Gram positive bacterial in a mammal in need thereof comprising administering to said mammal an effective amount of the peptide according to claim 1; and
treating said infections in said mammal.

9. A pharmaceutical composition comprising an effective amount of the peptide according to claim 1.

10. The pharmaceutical composition according to claim 9, in the form of injectable solution for systemic administration, or in the form of eyewash, mouth wash, ointment, or solution for topical administration.

11. A disinfectant and/or detergent preparation with antibacterial activity comprising the peptide according to claim 1.

12. A preservative for food, cosmetic or homeopathic products comprising the peptide according to claim 1.

* * * * *